(12) United States Patent
Che et al.

(10) Patent No.: US 7,648,977 B2
(45) Date of Patent: Jan. 19, 2010

(54) PHARMACEUTICAL COMPOSITION HAVING A RUTHENIUM OXALATO COMPOUND AND METHOD OF USING THE SAME

(75) Inventors: Chi-Ming Che, Hong Kong (CN); Raymond Wai-Yin Sun, Hong Kong (CN); Ella Lai-Ming Wong, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 705 days.

(21) Appl. No.: 11/256,175

(22) Filed: Oct. 24, 2005

(65) Prior Publication Data

US 2007/0105952 A1 May 10, 2007

(51) Int. Cl.
*A61K 31/555* (2006.01)
*A61K 31/28* (2006.01)

(52) U.S. Cl. ............... 514/185; 514/184; 514/492

(58) Field of Classification Search ........... 514/184, 514/185
See application file for complete search history.

(56) References Cited

OTHER PUBLICATIONS

Calvez et al. "Biochemical prevention and treatment of viral infection-A new paradigm in medicine for infection diseases," Virology Jornal, 2004, vol. 1, No. 12, pp. 1-6.*
Wong et al. "A mixed-valent ruthenium-oxo oxalato cluster Na7[Ru4(u3-O)4(C2O4)6] with potent anti-HIV activities," JACS, 2006, vol. 128, pp. 4938-4939.*
Erik De Clercq, Reviews in Medical Virology., vol. 10, pp. 255-277 (2000).
Carol Ezzell, Nature, vol. 329, p. 751 (1987).
http://www.aids.org.
Steven G. Deeks, The Lancet, vol. 362, pp. 2002-2011 (2003).
Orvig et al., Chemical Reviews, vol. 99, No. 9, pp. 2201-2203 (1999).
Abrams et al., Science, vol. 261, pp. 725-730 (1993).
Rosenberg et al., Nature, vol. 222, pp. 385-386 (1969).
Rhule et al., Chem. Rev., vol. 98, pp. 327-357 (1998).
Hill et al., J. Med. Chem., vol. 33, pp. 2767-2772 (1990).
Liang et al., Chem. Soc. Rev., vol. 33, pp. 246-266 (2004).
Wong et al., Chem. Commun., pp. 3544-3546 (2005).
Shin Aoki, Chem. Rev., vol. 104, pp. 769-787 (2004).
Sun et al., ChemBioChem., vol. 5, pp. 1293-1298 (2004).
Luedtke et al., ChemBioChem., vol. 3, pp. 766-771 (2002).
Mishra et al., Bioorganic & Medicinal Chemistry, vol. 9, pp. 1667-1671 (2001).
Che et al., Inorg. Chem., vol. 24, pp. 1359-1363 (1985).
Mercer et al., Inorganic Chemistry, vol. 4, pp. 1692-1695 (1965).
Otwinowski et al., "Processing of X-Ray Diffraction Data Collected in Oscillation Mode", Methods in Enzymology, vol. 276, pp. 307-326 (1997).
Zhang et al., Inorg. Chem., vol. 33, pp. 5262-5270 (1994).
Eberle et al., Journal of Virological Methods, vol. 40, pp. 347-356 (1992).
Gorczyca et al., Cancer Research, vol. 53, pp. 1945-1951 (1993).

* cited by examiner

*Primary Examiner*—Shengjun Wang
(74) *Attorney, Agent, or Firm*—Pabst Patent Group LLP (57) ABSTRACT

The present invention relates to a pharmaceutical composition comprising one or more of the following ruthenium oxalato compounds I, II, III and IV as an active ingredient. The pharmaceutical composition can be used for the treat- ment of viral-infected patients or prophylactic treatment of patients at risk from viral infection.

I

III

II

IV

11 Claims, 11 Drawing Sheets

Fig. 11

PHARMACEUTICAL COMPOSITION HAVING A RUTHENIUM OXALATO COMPOUND AND METHOD OF USING THE SAME

FIELD OF THE INVENTION

The present invention relates generally to a pharmaceutical composition having ruthenium oxalato compound. In addition, the present invention relates to the use of ruthenium oxalato compounds as potent anti-viral agents.

BACKGROUND OF THE INVENTION

Acquired Immunodeficiency Syndrome (AIDS) was first reported in the United States in 1981 and the AIDS epidemic shows great diversity in severity and timing worldwide. Human immunodeficiency virus type 1 (HIV-1), the causative agent of AIDS, is a retrovirus composed of RNA genetic material, which inhibits the human immune system from fighting off infection. Currently known anti-HIV agents fall into four major categories: (1) nucleoside reverse transcriptase inhibitors; (2) non-nucleoside reverse transcriptase inhibitors; (3) protease inhibitors; and (4) ribonucleotide reductase inhibitors (De Clercq et al. Rev. Med. Virol. (2000), 10, 255). The first clinically used drug for the treatment of HIV is azidothymidine (AZT) (Ezzell et al. Nature, (1987), 329, 751). AZT exerts its function by incorporating into the DNA chain, and results in interrupting chain elongation and impeding further replication of the genome (http://www.aids.org/). Although AZT and its cocktail regimens have shown promising effects on suppression of HIV-1 replication, drug-resistant HIV-1 as well as antiretroviral toxicity are still causes of growing clinical and public concern (Deeks S. G. Lancet (2003), 362, 2002).

The medicinal properties of metal-based compounds have been and continued to be an area of interest in new drug discovery (Orvig et al. Chem. Rev. (1999), 99, 2201-2203; Abrams et al. Science (1993), 261, 725-730). In the literatures, metal-based compounds have demonstrated clinical applications with the most notable example being cisplatin (Rosenberg et al. Nature (1969), 222, 385-386). While there have been extensive research on cytotoxic metal compounds, related studies on anti-viral metal-based compounds are under development. To our knowledge, there are several classes of metal-based compounds such as polyoxometalates (Rhule et al. Chem. Rev. (1998), 98, 327-357; Hill et al. J. Med. Chem. (1990), 33, 2767-2772), metallocyclams (Liang et al. Chem. Soc. Rev. (2004), 33, 246-266), vanadyl (Wong et al. Chem. Commun. (2005), 3544-3546), zinc (Aoki et al. Chem. Rev. (2004), 104, 769-787), and gold (Sun et al. ChemBioChem (2004), 5, 1293-1298) complexes known to display notable anti-HIV activities. However, examples regarding to the anti-viral activities of ruthenium-based compounds are limited (Luedtke et al. ChemBioChem (2002), 3, 766-771; Mishra et al. Bioorg. Med. Chem. (2001), 9, 1667-1671).

SUMMARY OF THE INVENTION

The present invention relates to structural characterization of a mixed-valence polyanionic ruthenium oxalato cluster that exhibited potent anti-HIV-1 activities by inhibiting HIV-1(BaL) replication in Hut/CCR5 cells, HIV-1(III$_B$) replication in GHOST/CXCR4 and normal human peripheral blood mononuclear cells (PBMC), and HIV-1 RT activity in in vitro studies. This ruthenium oxalato cluster showed low cytotoxicity toward the host cells as revealed by MTT assay. By means of TUNEL assay, this ruthenium oxalato compound was also found to exhibit cytoprotective activity toward HIV-1(III$_B$) infected Hut/CCR5 cells.

The present provides a novel ruthenium oxalato compound (2) capable of inhibiting HIV-1(BaL) replication in Hut/CCR5 cells, HIV-1(III$_B$) replication on GHOST/CXCR4 and PBMC and HIV-1 RT inhibitory activity in in vitro studies. This novel metal-based compound exhibited low cytotoxicity to the host cells (as observed by MTT assay) and showed cytoprotective activity toward HIV-1 infected Hut/CCR5 cells (as observed by TUNEL assay). The present invention provides an application of ruthenium oxalato compounds, a unique class of ruthenium-based compound, as anti-HIV agents as evidenced by the potent inhibitory activity on HIV-infected Hut/CCR5, GHOST/CXCR4, and PBMC cells, and HIV-1 RT by administering to a patient in need thereof a composition comprising an effective amount of ruthenium oxalato compound.

DETAILED DESCRIPTION OF THE INVENTION

The present invention relates to a ruthenium oxalato compound, which can be used as anti-viral agents. For example, one or more ruthenium oxalato compounds can be provided which can have potent inhibitory effect on HIV-1(BaL) replication in Hut/CCR5 cells, HIV-1 (III$_B$) replication on GHOST/CXCR4 and PBMC cells, and HIV-1 RT inhibitory activity in in vitro studies. The ruthenium oxalato compound can have a low cytotoxicity toward the host cells as revealed by MTT assay. By means of TUNEL assay. The ruthenium oxalato compound can also exhibit cytoprotective activity toward HIV-1(III$_B$) infected Hut/CCR5 cells.

The present invention also relates to a method of using one or more of the ruthenium oxalato compounds as antiviral agents. In one embodiment, a method is provided for inhibition of HIV activity by administering, such as to a patient or cell-based assay, a composition comprising an effective amount of a ruthenium oxalato compound. The cell referred to can be that of a kind of animal of the kingdom Animalia. Non-limiting examples of the cell include Hut/CCR5, GHOST/CXCR4 and PBMC.

The amount of the ruthenium oxalato compound in the composition can vary. In one exemplary embodiment, the effective amount of the ruthenium oxalato compound can be from 100 ng/kg to 100 mg/kg, such as when the composition is used on a patient. For example, the ruthenium oxalato compound can be 190 ng/kg, 50 μg/kg, 500 μg/kg, or 5 mg/kg, such as depending on a patient's condition. In another exemplary embodiment, the effective amount of the ruthenium oxalato compound can be from 1 nM to 1 mM, such as when the composition is used on a cell-based assay. For example, the ruthenium oxalato compound can be 1.9 nM, 500 nM, 5 μM, and 50 μM.

The ruthenium oxalato compound of the present invention can be represented by structural formula I, II, III, or IV, or a pharmaceutically acceptable salt thereof:

The ruthenium oxalato compound of the present invention affords various antiviral effects. In one exemplary embodiment, the ruthenium oxalato compound I, II, III, or IV, or a pharmaceutically acceptable salt thereof can inhibit HIV-1 (BaL) replication in Hut/CCR5 cells in in vitro studies. In another exemplary embodiment, the ruthenium oxalato compound I, II, III, or IV, or a pharmaceutically acceptable salt thereof can inhibit HIV-1($III_B$) replication in GHOST/CXCR4 cells in in vitro studies. In another exemplary embodiment, the ruthenium oxalato compound I, II, III, or IV, or a pharmaceutically acceptable salt thereof can inhibit HIV-1($III_B$) replication in PBMC cells in in vitro studies. In another exemplary embodiment, the ruthenium oxalato compound I, II, III, or IV, or a pharmaceutically acceptable salt thereof can inhibit HIV-1 RT activity in in vitro studies. In another exemplary embodiment, the ruthenium oxalato compound I, II, III, or IV can exhibit low cytotoxicity and have cytoprotective activity toward HIV-1 infected Hut/CCR5 cells.

I. Definition

Pharmaceutical composition and the use of a ruthenium oxalato compound for combating virus are provided herein. The pharmaceutical composition contains a ruthenium oxalato compound in an amount effective to inhibit the activity of reverse transcriptase and the anti-proliferation of virus.

It will be understood that the ruthenium oxalato compound will not form a charge neutral complex. For instance, the net positive charge on the cationic metal can be less than the absolute net negative charge of the coordinated oxalato ligand. In view of this, there will be least one cation or counter-ion coordinated to the metal compound for charge neutralization. As used herein, the phrase "pharmaceutically acceptable salt" described herein includes salts formed from charged metal complex and the cation or counter-ion.

As used herein, the term "cation" or "counter-ion" described herein refers to the positively charged group coordinated to the negatively charged oxalate ligand of the ruthenium oxalato compound. Non-limiting examples of cations include Li, Na and K.

As used herein, the ruthenium oxalato compound can exist as a single molecule or aggregated molecules.

As used herein, the phrase of "pharmaceutically acceptable carrier" means approved by a regulatory agency of the Federal or a state government or listed in the U.S. Pharmacopoeia or other generally recognized pharmacopoeia for use in animals, mammals, and more particularly in humans. Non-limiting examples of pharmaceutically acceptable carriers include liquids, such as water and oils, including those of petroleum, animal, vegetable, or synthetic origin. Water is a preferred vehicle when the compound of the present invention is administered intravenously. Saline solutions and aqueous dextrose and glycerol solutions can also be employed as liquid vehicles, particularly for injectable solutions.

As used herein, the term "patient" refers to any member of the kingdom Animalia. Non-limiting examples of animals include a cow, monkey, horse, sheep, pig, cat, dog, mouse, rat, rabbit, and guinea pig and most preferably human.

As noted above, the present invention relates to compositions useful for the inhibition of viral activity in virus-infected cells. Non-limiting examples of virus include human hepatitis A virus (HAV), human hepatitis B virus (HBV), human hepatitis C virus (HCV), severe acute respiratory syndrome associated coronavirus (SARS-CoV), herpes simplex virus, human papillomavirus, human herpesvirus, influenza virus, simian immunodeficiency virus (SIV), and most preferably human immunodeficiency virus (HIV).

As used herein, the term "PBMC" described herein refers to normal human peripheral blood mononuclear cells.

As used herein, the term "HIV-1 RT" described herein refers to HIV-1 reverse transcriptase.

As used herein, the term "TUNEL" described herein refers to Terminal Uridyl-Nucleotide End Labeling.

As used herein, the term "GSH" described herein refers to reduced glutathione.

As used herein, the term "MTT assay" described herein refers to (3-[4,5-dimethylthiazol-2-yl]-2,5-diphenyltetrazolium bromide) assay.

As used herein, the term "AZT" described herein refers to azidothymidine.

II. Synthesis of Ruthenium Oxalato Compound

In general, the ruthenium oxalato compounds of this invention were discovered as a new class of substance that can be made according to a modification of a procedure for preparing $Na_3[Ru(ox)_3]$ (1) (Che et al. Inorg. Chem. (1985), 24, 1359). $K_2[RuCl_5(OH_2)]$ and oxalic acid were stirred in an aqueous medium for 2 weeks at room temperature. During the course of the reaction, a gradual color change from dark black to deep brown was observed. After 2 weeks, the pH of the reaction mixture was changed to alkaline (ca. pH=10) by adding $NaHCO_3$.

In this invention, the compositions described herein are ruthenium oxalato clusters having the following structure IV:

IV

An exemplary synthetic ruthenium oxalato cluster of formula IV is given below:

2

Ruthenium oxalato cluster $Na_7[Ru_4(\mu_3-O)_4(C_2O_4)_6]$ (2) was obtained as a dark green solid and as the sodium salt in 10% yield. A small amount of $Na_3[Ru(ox)_3]$ (1) afforded as a light brown solid was also obtained. Due to differences in solubility of 1 and 2 in water, the latter cluster preferentially precipitated out by slow diffusion of acetone into a solution of water containing 2. Repeated recrystallization removed undesired 1.

III. Anti-HIV Activity of Ruthenium Oxalato Cluster

The ruthenium oxalato cluster $Na_7[Ru_4(\mu_3-O)_4(C_2O_4)_6]$ (2) described in this invention exhibited potent inhibitory effect on HIV-1(BaL) replication in Hut/CCR5 cells, HIV-1 ($III_B$) replication in GHOST/CXCR4 and PBMC cells, and HIV-1 RT inhibitory activity in in vitro studies. This class of ruthenium-based clusters also exhibited low cytotoxicity and showed cytoprotective activity toward HIV-1 infected Hut/CCR5 cells as observed by TUNEL assay. The present invention describes the first application of a polyanionic ruthenium oxalato cluster, a class of metal-based clusters, as antiviral agents, demonstrating potent anti-HIV inhibitory activity.

Non-limiting examples of cells for antiviral studies include but not limited to Hut/CCR5, GHOST/CXCR4 and PBMC cells.

The invention relates to ruthenium oxalato cluster $Na_7[Ru_4(\mu_3-O)_4(C_2O_4)_6]$ (2) demonstrating inhibition of HIV-1(BaL) replication in Hut/CCR5 cells, HIV-1($III_B$) replication in GHOST/CXCR4 and PBMC cells, and HIV-1 RT inhibitory activity in in vitro studies. This class of metal-based clusters also exhibited low cytotoxicity and showed cytoprotective activity toward HIV-1 infected Hut/CCR5 cells as observed by TUNEL assay.

IV. Examples

The following examples are set forth to assist in understanding the invention and should not be construed as specifically limiting the invention described and claimed herein. Such variations of the invention, including substitution of all equivalents now known or later developed, which would be within the purview of those skilled in art, and changes in formulations or minor changes in experimental design, fall within the scope of present invention.

Instrumentation. All absorption spectra and MTT assays were recorded on a Perkin-Elmer Lambda 900 and Perkin-Elmer Fusion α-FP spectrophotometer. Positive ion FAB and EI mass spectra were recorded on a Finnigan MAT95 mass spectrometer. Electrospray ionization mass spectrometry (ESI-MS) was performed on a Micromass Q-TOF² spectrometer. ¹H NMR spectra were recorded on Brucker DPX-300 or DPX-400 NMR spectrometers. Magnetic measurements were performed on a Quantum Design SQUID magnetometer. TUNEL flow cytometric analysis was performed with a Coulter EPICS flow cytometer (Coulter, Miami, Fla.) equipped with 480 long, 525 band and 625 long pass mirrors. Samples were excited by 15 mW air-cool argon convergent laser at 488 nm. Fluorescence signal were manipulated with Coulter Elite 4.0 software (Coulter) and were analyzed by Winlist 1.04 and Modfit 5011 software (verity Software House, Topsham, Me.).

Materials. All chemicals were of analytical grade and purchased from Sigma-Aldrich Chemical Co. unless otherwise noted. Analytical grade organic solvents and Milli-Q water were used throughout the experiments. Ruthenium trichloride was purchased from Strem. Preparation of $K_2[RuCl_5$ (OH$_2$)] was achieved by a methodology along the lines of that described in Mercer and Buckley *Inorg. Chem.* (1965), 4, 1692.

HIV-1(BaL) and HIV-1 (III$_B$) stocks (300 ng/mL of p24 protein), Hut/CCR5 and GHOST/CXCR4 cells were gifts from Dr. D. Tao (Institute of Molecular Medicine, University of Oxford, UK). Peripheral blood mononuclear cells (PBMC) were prepared from buffy coat obtained from the Hong Kong Red Cross Blood Transfusion Service.

Each unit of the buffy coat prepared from whole blood (450 mL) contained approximately 5×10$^8$ cells. To isolate the PMBC, the buffy coat (15 mL) was transferred to a centrifuge tube (50 mL) under sterile conditions and diluted with RPMI culture medium in a 1:1 (v/v) ratio. Ficoll® solution (15 mL) was slowly added to the diluted blood and the mixture was centrifuged at 800 rpm for 25 min. at room temperature. The PBMC at the interface were washed five times with cold RPMI culture medium. The washed PBMC were spun first at 500 rpm for 7 min., followed at 250 rpm for 7 min. and finally at 200 rpm to obtain a cell pellet. The PBMC were re-suspended in ammonium chloride lysis buffer (ACK buffer) and incubated at room temperature for 5 min. to lyse the remaining red blood cells. Hut/CCR5 cells, GHOST/CXCR4 cells and PBMC were maintained in RPMI 1640 medium (Life Technologies, Inc.) supplemented with fetal bovine serum (10%, v/v) and L-glutamine (2 mM). Penicillin (100 U/mL) and streptomycin (100 µg/mL) were added to all media, except for PBMC. The whole cell cultures were incubated at 37° C. in a 5% CO$_2$/95% air humidified atmosphere and sub-cultured twice weekly (except for PBMC).

The identity of complexes 1 and 2 were characterized by microanalysis (elemental analyses), X-ray crystallography, FAB-MS, UV-visible spectroscopy (see FIGS. 1-6).

Example 1

Procedure for Preparation of Ruthenium Oxalato Cluster Na$_7$[Ru$_4$(µ$_3$-O)$_4$(C$_2$O$_4$)$_6$] (2)

Example 1 describes the preparation and characterization of illustrative ruthenium oxalato cluster Na$_7$[Ru$_4$(µ$_3$-O)$_4$(C$_2$O$_4$)$_6$] (2).

K$_2$[RuCl$_5$(OH$_2$)] (1 g, 2.7 mmol) and oxalic acid (1.15 g, 12.8 mmol) were stirred in deionized water (10 mL). Slow warming was required to completely dissolve oxalic acid in the aqueous solution. The reaction mixture was stirred at room temperature for 2 weeks, in which a color change from dark black to deep brown was observed. On completion, the reaction mixture was heated to reflux for 2 h and NaHCO$_3$ was added in small aliquots. Addition of NaHCO$_3$ (ca. 2-3 g) was stopped when no more bubbles were observed. The mixture was continuously refluxed for 3 h and cooled to room temperature. Dark green crystals of 2 were obtained by slow diffusion of acetone to the aqueous reaction mixture. Under light microscope, a small amount of a light brown crystalline solid in addition to dark green crystals of 2, which was characterized as Na$_3$[Ru(ox)$_3$] (1) by X-ray crystallography was obtained. Contaminant 1 was removed by repeated recrystallization.

Na$_7$[Ru$_4$(µ$_3$-O)$_4$(C$_2$O$_4$)$_6$] (2): Yield: 10%. UV-vis (H$_2$O): $\lambda_{max}$/dm$^3$ mol$^{-1}$ cm$^{-1}$): 266 (8100), 328 (3760, sh), 800 (1300, broad). ESI-MS -ve (Q-TOF): m/z 1003.42 [Ru$_4$O$_4$(C$_2$O$_4$)$_6$.H$_6$]$^-$, 1025.43 [Ru$_4$O$_4$(C$_2$O$_4$)$_6$.H$_5$.Na]$^-$, 1047.40 [Ru$_4$O$_4$(C$_2$O$_4$)$_6$.H$_4$.Na$_2$]$^-$, 1069.42 [Ru$_4$O$_4$(C$_2$O$_4$)$_6$.H$_3$.Na$_3$]$^-$, 1091.40 [Ru$_4$O$_4$(C$_2$O$_4$)$_6$.H$_2$.Na$_4$]$^-$, 1113.41 [Ru$_4$O$_4$(C$_2$O$_4$)$_6$.H.Na$_5$]$^-$, 1135.40 [Ru$_4$O$_4$(C$_2$O$_4$)$_6$.Na$_6$]$^-$.

Anal. Calcd. for C$_{12}$O$_{28}$Ru$_4$Na$_7$ (%): C, 12.45; O, 38.7; H, 0; N, 0. Found: C, 12.80; O, 38.42; H, 0.02; N, 0.01.

X-ray Crystallography. Crystals of 1 and 2 were obtained from diffusion of acetone to the aqueous reaction mixture containing 1 and 2 at room temperature (see FIGS. 1-2). A brown crystal of dimensions 0.4×0.25×0.2 mm of 1 and a deep green crystal of dimensions 0.25×0.2×0.1 mm of 2 were mounted in a glass capillary used for data collection at −20° C. on a MAR diffractometer with a 300 mm image plate detector using graphite monochromatized Mo-K$_\alpha$ radiation ($\lambda$=0.71073 Å).

Data collection was made with 2° oscillation step of φ, 480 seconds exposure time and scanner distance at 120 mm. 100 images were collected. The images were interpreted and intensities integrated using program DENZO (Otwinowski and Minor, In *Processing of X-ray Diffraction Data Collected in Oscillation Mode, Methods in Enzymology*, C. W. Carter, Sweet Jr. & R. M., Eds.; Academic Press: (1997); Vol. 276, pp. 307). The structure was solved by direct methods employing SHELXS-97 program (Sheldrick, *SHELX*97. *Programs for Crystal Structure Analysis* (*Release* 97-2), University of Goetingen, Germany, (1997)) on a PC. Step-scanned X-ray powder diffraction data of 2 was collected on a Phillips PW3710 powder diffractometer by using graphite-monochromated Cu$_{K\alpha}$ ($\lambda$=1.5406 Å, Ni-filter) radiation, operated at 40 kV and 30mA (see FIG. 3).

Sample was unpacked and reloaded onto the sample holders for replication data collections to minimize the systematic errors from particle statistics and preferred orientation of the samples. All samples were free of known oxides and metal impurities checked by ICCD database match search. Data collection parameters of 2-60° (2θ), step size=0.02°, and scan speed=0.004° s$^{-1}$ were used to optimize the count statistics and peak shape profiles.

Example 2

Magnetic Measurements of Na$_7$[Ru$_4$(µ$_3$-O)$_4$(C$_2$O$_4$)$_6$] (2)

Example 2 describes magnetic properties and mixed-valence oxidation state of Na$_7$[Ru$_4$(µ$_3$-O)$_4$(C$_2$O$_4$)$_6$] (2).

The magnetic properties and temperature magnetic susceptibility of 2 were performed on Quantum Design SQUID Magnetometer. The Quantum Design magnetometer (MPMS-5s) is equipped with a superconductor magnet (5 Tesla), AC susceptibility measurement and Reciprocating Sample Option (RSO). The temperature range is 1.8K<=T<=400K, with a furnace of 300K<=T<=800K. Magnetic measurements: Magnetization as a function of temperature and magnetic field. The sample crystals were grinded to powder and located in a holder for measurement.

Na$_7$[Ru$_4$(µ$_3$-O)$_4$(C$_2$O$_4$)$_6$] (2) of this invention shows no ferromagnetic and antiferromagnetic behavior. Using the Curie Law, the Curie Constant for 2 is 0.347 cm$^3$ K mol$^{-1}$ and magnetic moment of 1.67 µ$_B$. This corresponds to 1 unpaired electron (calculated S=½, µ$_{eff}$=1.73 µ$_B$) and suggests that the four ruthenium atoms do not have the same oxidation state. In conjunction with X-ray analysis, the mixed-valence oxidation state of (III, III, III, IV) for 2 is deduced (see FIG. 5). Mixed valency in 2 is also been supported by a broad absorption band observed in the UV-vis spectrum of 2 at around 800 nm ($\epsilon$=1300 dm$^3$ mol$^{-1}$ cm$^{-1}$) in H$_2$O that is attributed to the intervalence band (see FIG. 6). Such intervalence band has also been observed in other ruthenium systems with oxo bridges or carboxylate ligands. (Shepherd *Inorg. Chem.* (1994), 33, 5262).

Example 3

Stability Studies of $Na_7[Ru_4(\mu_3-O)_4(C_2O_4)_6]$ (2)

Example 3 describes the results of stability studies for $Na_7[Ru_4(\mu_3-O)_4(C_2O_4)_6]$ (2).

The UV-vis absorption spectra of 2 were monitored over 7 days in aqueous solution. Its stability in physiological relevant medium (in the presence of 2 mM GSH aqueous solution) was also monitored by UV-vis spectroscopy.

No observable changes in the spectra were observed for 2 when upon standing in $H_2O$ and 2 mM GSH aqueous solution for 7 days. This shows that 2 is stable in both $H_2O$ and physiological medium and that the cluster framework is intact in solution. This provides the opportunity to understanding its mode of action in biological systems.

Example 4

Inhibition of HIV-1(BaL) Replication in Hut/CCR5 Cells

Example 4 describes the procedure employed to examine the inhibitory effects of $Na_7[Ru_4(\mu_3-O)_4(C_2O_4)_6]$ (2) on HIV-1(BaL) replication in Hut/CCR5 cells and the results of these studies.

Stock solutions (10 mM) of $Na_7[Ru_4(\mu_3-O)_4(C_2O_4)_6]$ (2) were prepared in sterile water and diluted to desired concentration in growth medium. Hut/CCR5 cells in 24-well plate ($5 \times 10^5$ cells/well) were pretreated with compounds (400 µL) for an hour at 37° C. and subsequently infected in triplicate with a panel of CCR5-tropic HIV-1 isolates (with the addtion of 5 µL of HIV-1 stock to each well, total p24 content=1500 pg) for 3 h. Following infection, the cells were washed to remove residual viral inoculums and cultured in the presence of compounds (400 µL) for 3 or 7 days. Culture supernatants were harvested and viral replication was measured by determination of viral p24 antigen concentration by ELISA (HIV-1 p24 antigen Kit, Beckman Coulter). Compounds were tested in triplicate at 3 concentrations ranging from 0.5-50 µM. AZT and $RuCl_3$ were also examined as reference standards.

Figure 1:
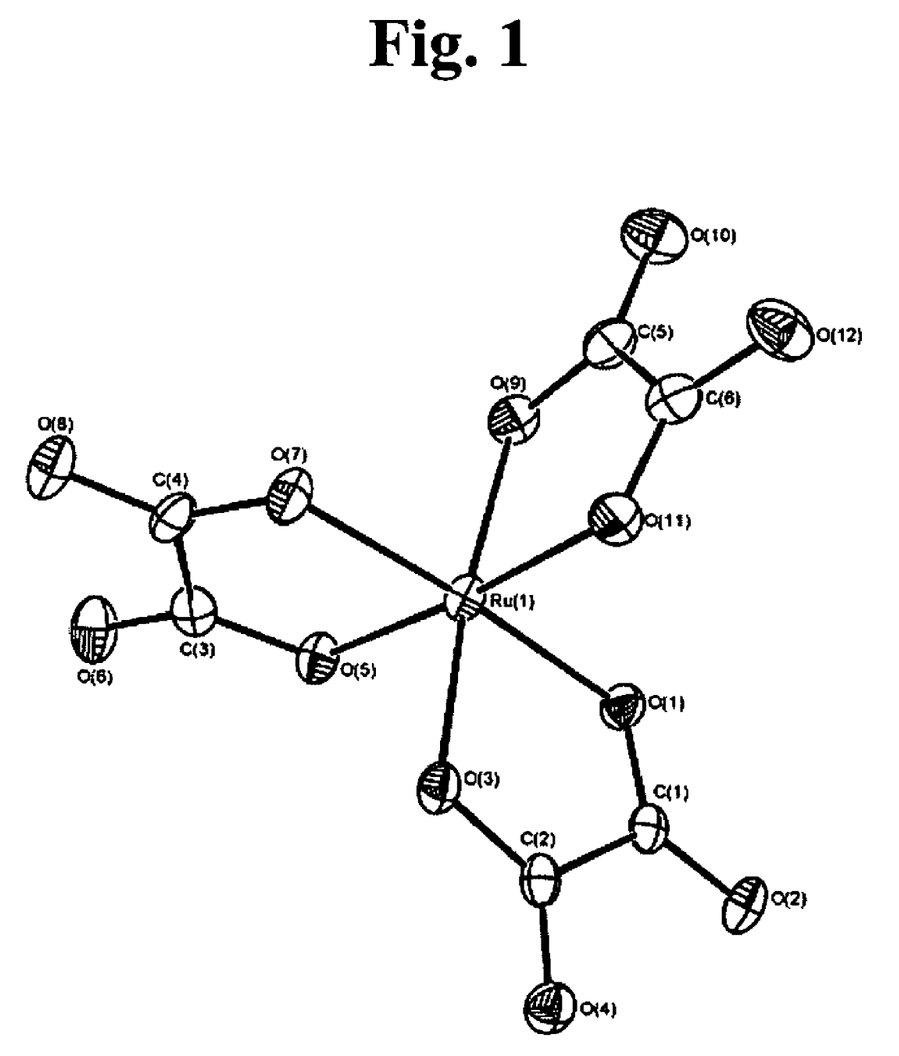
FIG. 1 illustrates a perspective view of Na$_3$[Ru(ox)$_3$] (1). Thermal ellipsoids are drawn at the 30% probability level.
Figure 2:
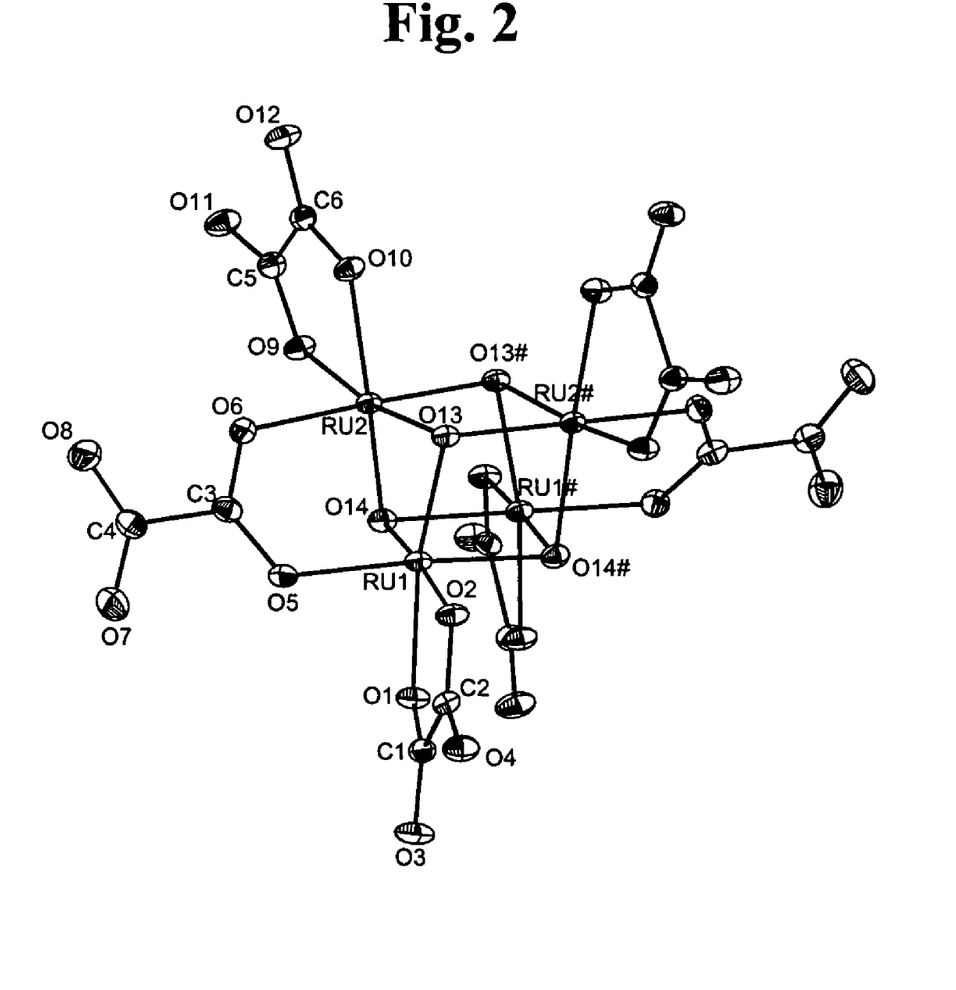
FIG. 2 illustrates a perspective view of Na$_7$[Ru$_4$($\mu_3$-O)$_4$(C$_2$O$_4$)$_6$] (2) of this invention. Sodium counterions and water have been omitted for clarity. Thermal ellipsoids are drawn at the 30% probability level.
Figure 3:
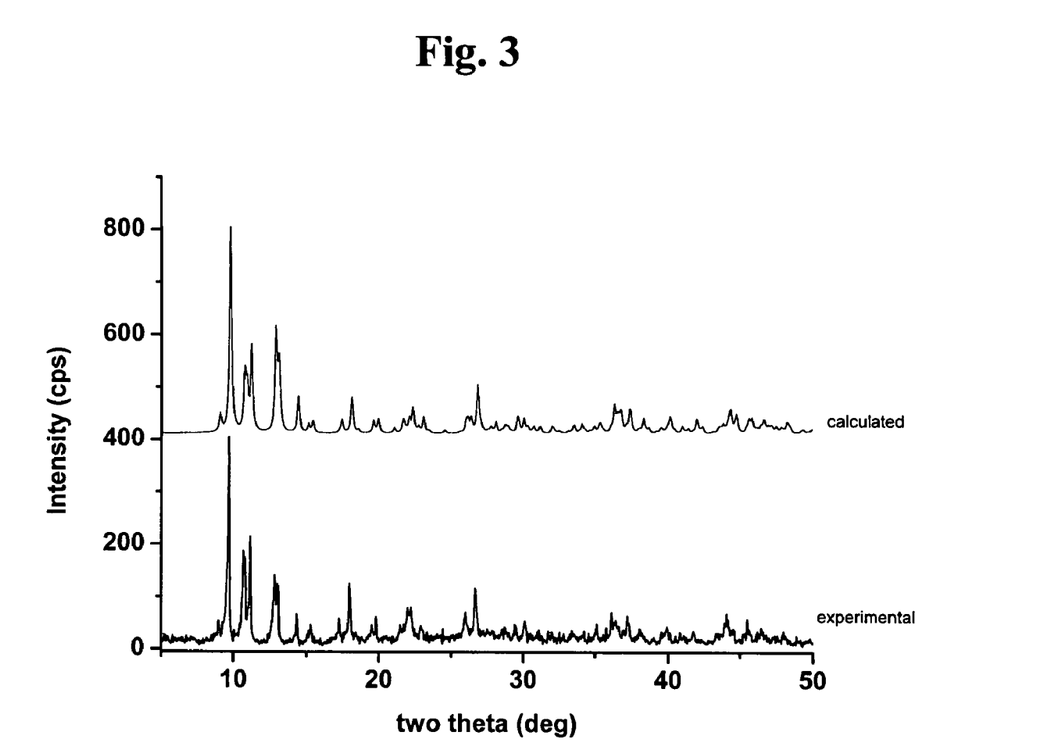
FIG. 3 illustrates the simulated and experimental powder X-ray diffraction patterns for Na$_7$[Ru$_4$($\mu_3$-O)$_4$(C$_2$O$_4$)$_6$] (2).
Figure 4:
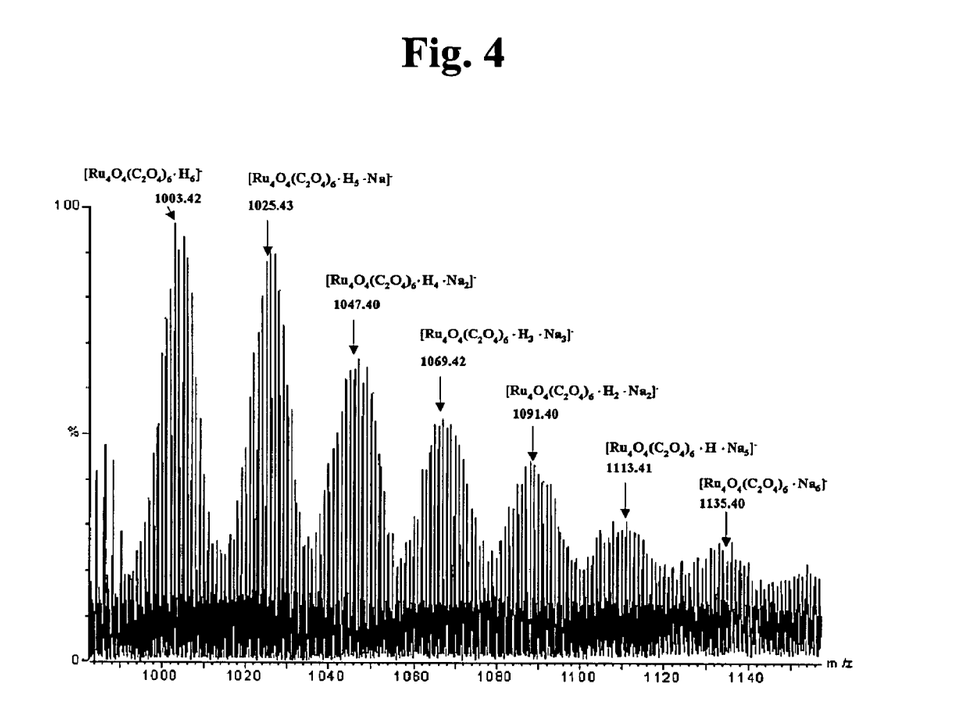
FIG. 4 illustrates the Q-TOF ESI-MS spectrum of Na$_7$[Ru$_4$($\mu_3$-O)$_4$(C$_2$O$_4$)$_6$] (2) (with addition of TFA and negative ion mode).
Figure 5:
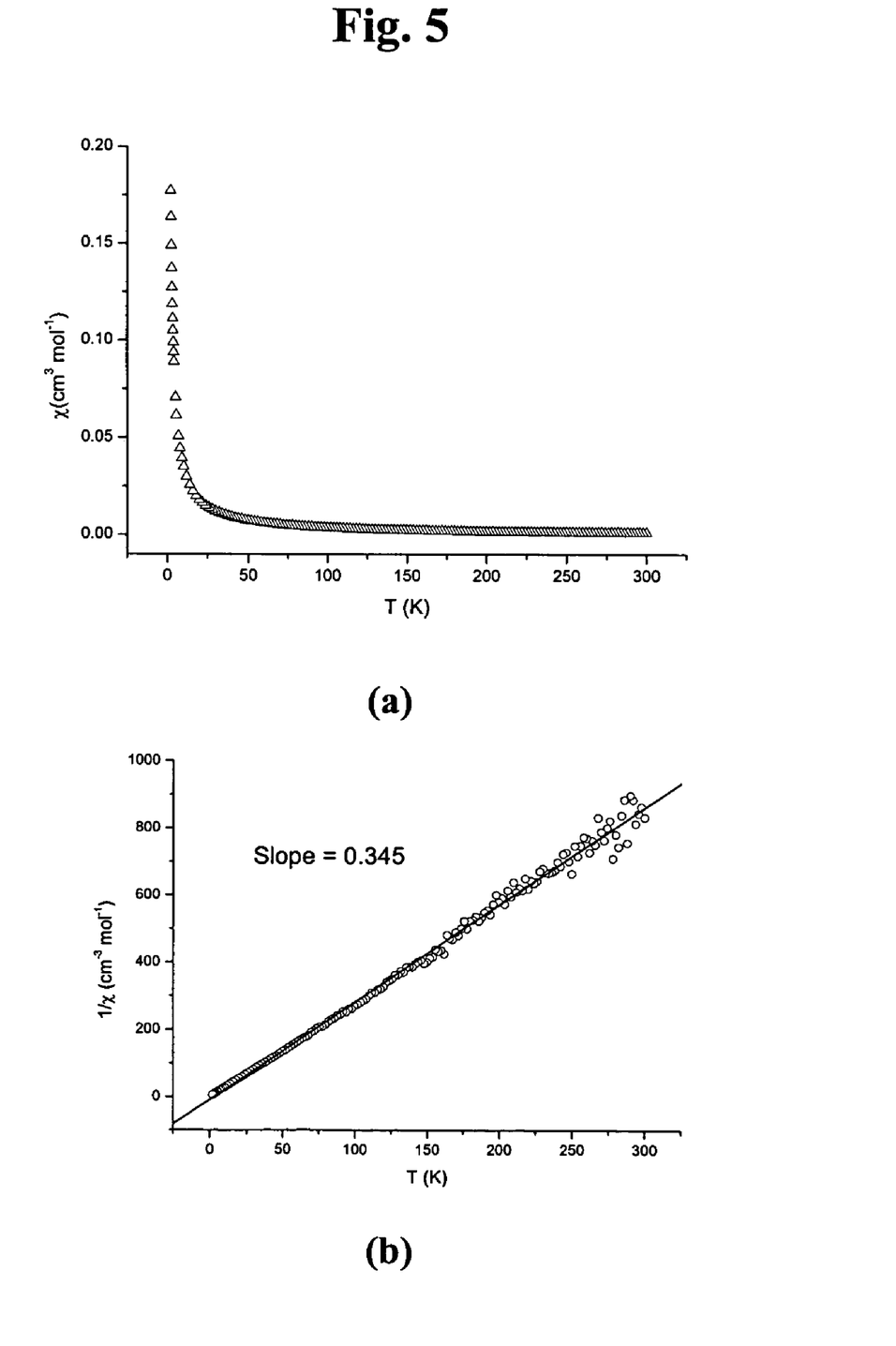
FIG. 5 illustrates the temperature-dependent magnetic susceptibility of Na$_7$[Ru$_4$($\mu_3$-O)$_4$(C$_2$O$_4$)$_6$] (2). Temperature dependent $\chi_m$ (a) plot of $\chi$ vs T and (b) plot of 1/$\chi$ vs T.
Figure 6:
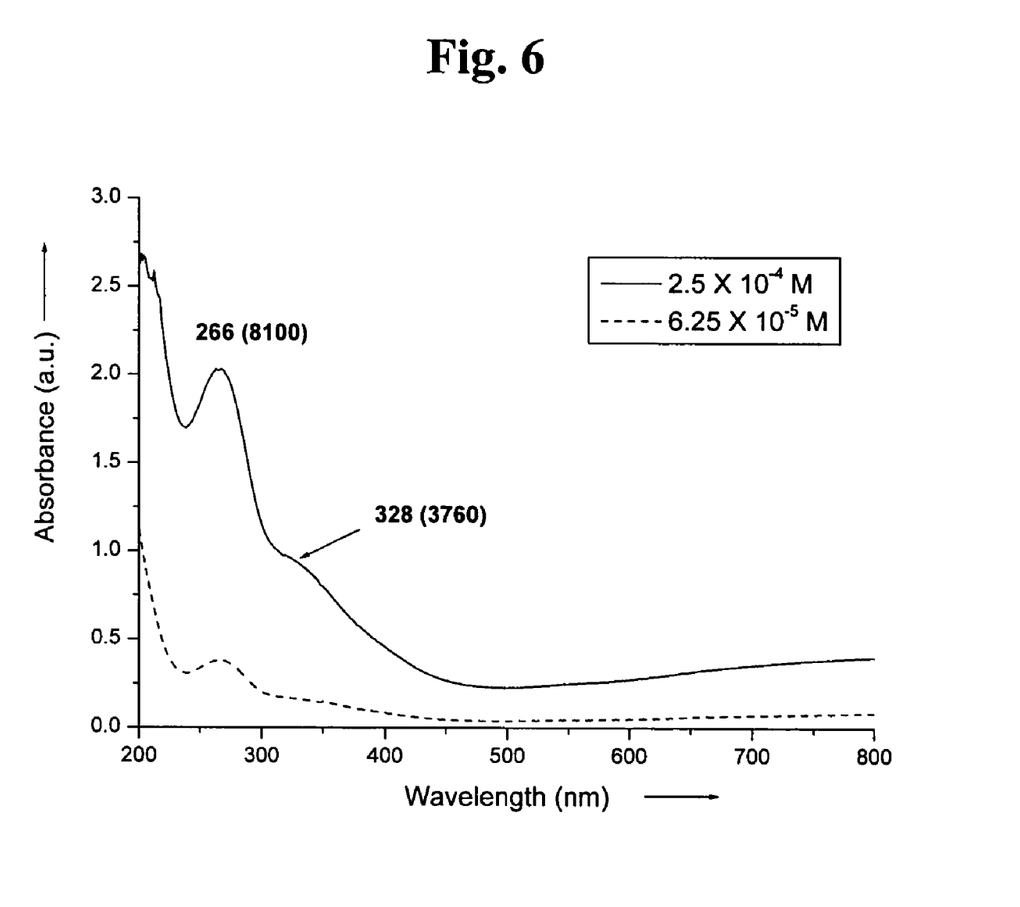
FIG. 6 illustrates the UV-vis spectra of Na$_7$[Ru$_4$($\mu_3$-O)$_4$(C$_2$O$_4$)$_6$] (2) in aqueous solution.
Figure 7:
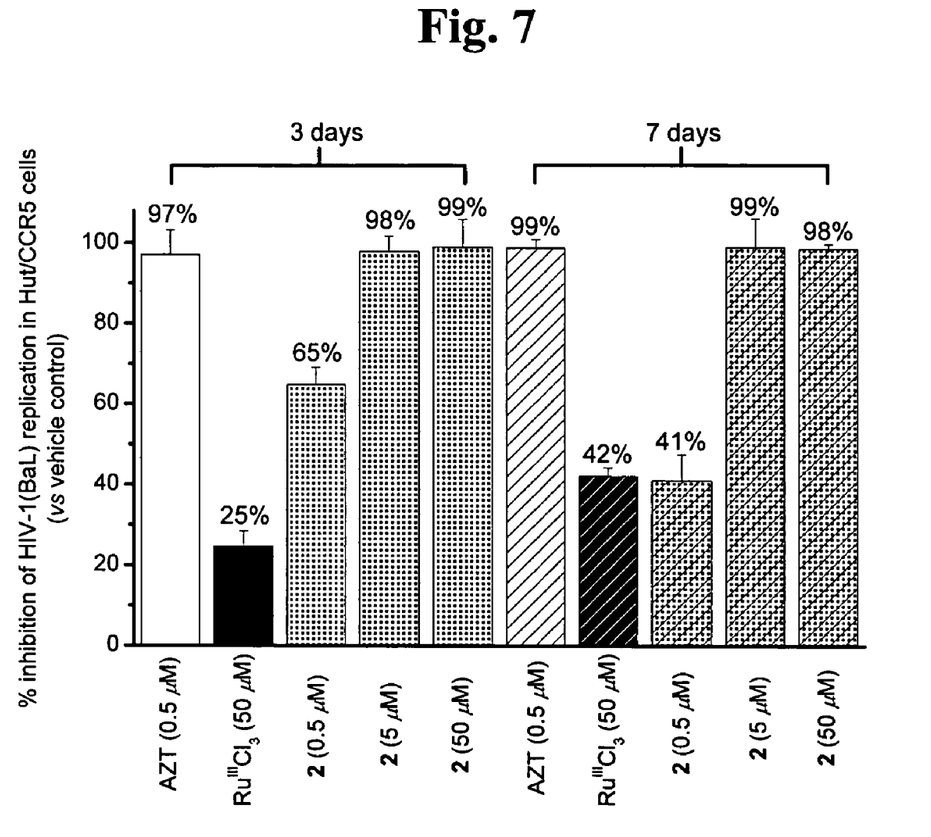
FIG. 7 illustrates the percentage inhibition of HIV-1(BaL) replication by Na$_7$[Ru$_4$($\mu_3$-O)$_4$(C$_2$O$_4$)$_6$] (2) in Hut/CCR5 cells in (a) 3-day and (b) 7-day incubation period.

$Na_7[Ru_4(\mu_3-O)_4(C_2O_4)_6]$ (2) of this invention inhibited HIV-1(BaL) replication in Hut/CCR5 cells (see FIG. 7).

Example 5

Inhibition of HIV-1 ($III_B$) Replication in GHOST/CXCR4 and PBMC Cells

Example 5 describes the procedures employed to examine the inhibitory effects of $Na_7[Ru_4(\mu_3-O)_4(C_2O_4)_6]$ (2) on HIV-1($III_B$) replication in GHOST/CXCR4 and PBMC cells and the results of these studies.

Stock solutions (10 mM) of 2 were prepared in sterile water and diluted to desired concentration in growth medium. GHOST/CXCR4 and PBMC cells in 24-well plate ($5 \times 10^5$ cells/well) were pretreated with compounds (400 µL) for an hour at 37° C. and subsequently infected in triplicate with a panel of CCR5-tropic HIV-1 isolates (with the addition of 5 µL of HIV-1 stock to each well, total p24 content=1500 pg) for 3 h. Following infection, the cells were washed to remove residual viral inoculums and cultured in the presence of compounds (400 µL) for 3 or 7 days. Culture supernatants were harvested and viral replication was measured by determination of viral p24 antigen concentration by ELISA (HIV-1 p24 antigen Kit, Beckman Coulter). Compounds were tested in triplicate at 3 concentrations ranging from 0.5-50 µM. AZT was also examined as a reference standard.

Figure 8:
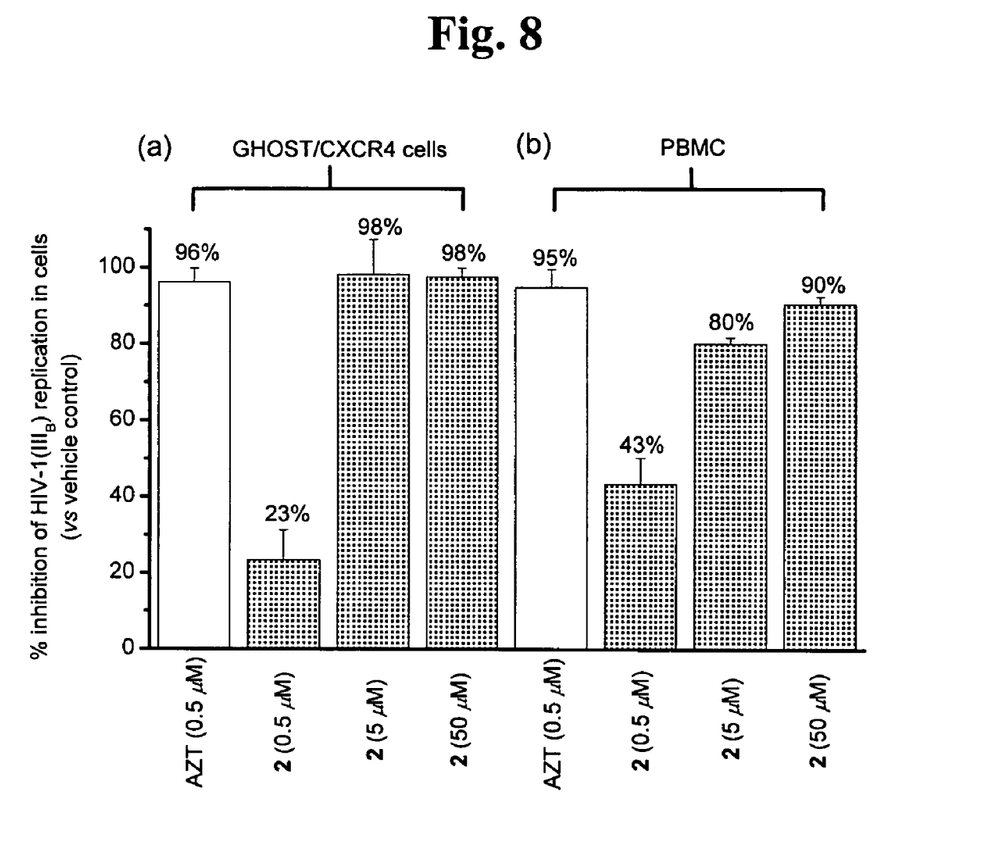
FIG. 8 illustrates the percentage inhibition of HIV-1(III$_B$) replication by Na$_7$[Ru$_4$($\mu_3$-O)$_4$(C$_2$O$_4$)$_6$] (2) in (a) GHOST cells and (b) PBMC in a 7-day incubation period.

$Na_7[Ru_4(\mu_3-O)_4(C_2O_4)_6]$ (2) of this invention inhibited HIV-1(BaL) replication in GHOST/CXCR4 and PBMC cells (see FIG. 8).

Example 6

Inhibition of HIV-1 RT Activity

Example 6 describes the procedures employed to examine the inhibitory effect of $Na_7[Ru_4(\mu_3-O)_4(C_2O_4)_6]$ (2) on HIV-1 RT activity and the results of these studies.

The inhibitory effect of different compounds on HIV-1 RT activities were assayed using a commercial assay kit (Reverse Transcriptase Assay, Chemiluminescent, Roche). Complex 2 and AZT-TP were first dissolved in PBS (1.3 µL) and mixed with a set of HIV-1 RT in lysis buffer (2 ng, 128.7 µL) at 37° C. (30 min.). The ELISA assays were conducted by following the manufacturer's instructions (Eberle and Seibl *J. Virol. Methods* (1992), 40, 347). In general, the indicated components were added to the corresponding wells of the microtitre plate from the kit and incubated for 1 h at 37° C. The solution in each well was then completely removed and the wells were rinsed five times with 250 µL of washing buffer per well. During each washing step, the washing buffer was left in the wells for a minimum of 30 seconds. The microtitre plate modules were covered and dried with a blotting paper, followed by the incubation with anti-DIG-POD working dilution was added (200 µL per well) for 1 h at 37° C. The solution was discarded followed by the washing and drying steps as described above. The POD substrate was added (200 µL per well) and was incubated at room temperature for 15 min. The chemiluminescent signal was measured and quantified using a microtitre plate chemiluminescence reader. The HIV-1 RT activities were evaluated based on percentage luminescence of the solutions relative to the negative control (untreated population).

Figure 9:
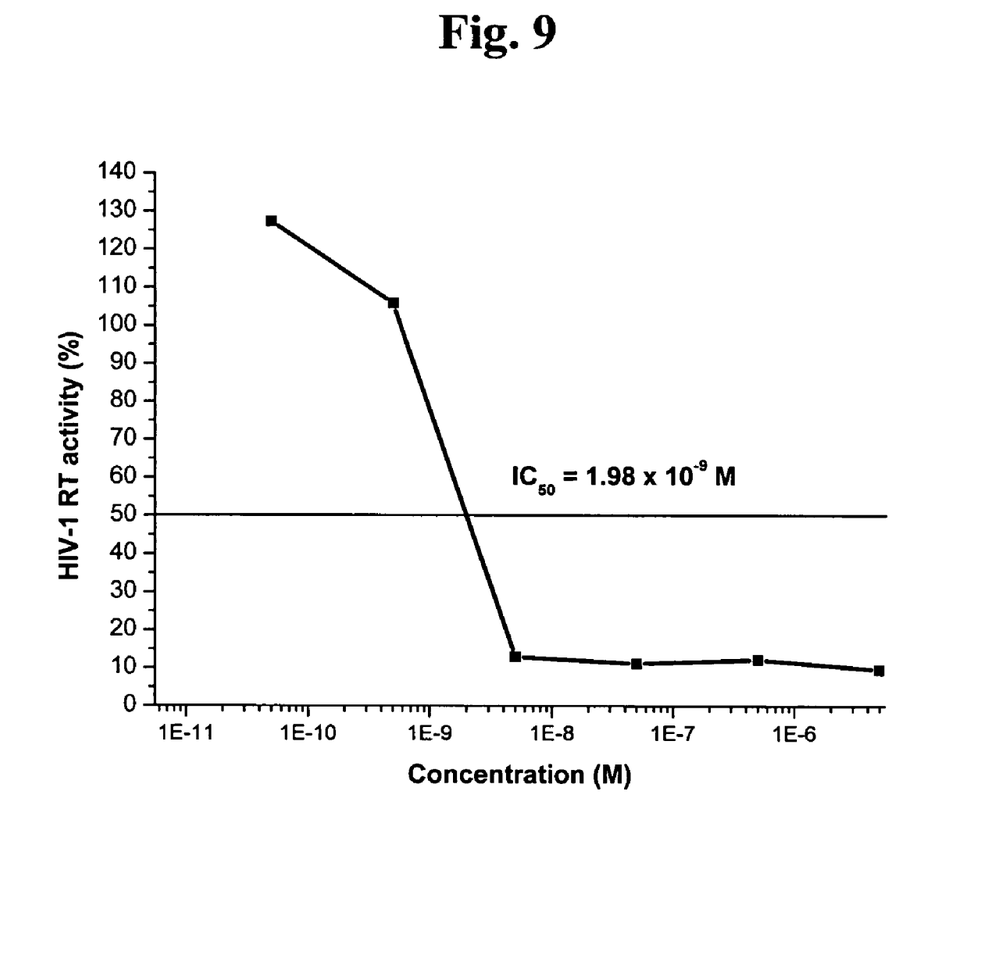
FIG. 9 illustrates the inhibition of HIV-1 RT activity by Na$_7$[Ru$_4$($\mu_3$-O)$_4$(C$_2$O$_4$)$_6$] (2).

$Na_7[Ru_4(\mu_3-O)_4(C_2O_4)_6]$ (2) of this invention inhibited HIV-1 RT activity (see FIG. 9).

Example 7

Cytoprotective Activity of $Na_7[Ru_4(\mu_3-O)_4(C_2O_4)_6]$ in HIV-1 Infected Hut/CCR5 Cells Example 7 describes the procedures employed to examine the cytoprotective effects of $Na_7[Ru_4(\mu_3-O)_4(C_2O_4)_6]$ (2) on HIV-1 infected Hut/CCR5 cells and the results of these studies.

The TUNEL reaction preferentially labels DNA strand breaks generated during apoptosis. This is done by labeling DNA strand breaks by terminal deoxynucleotidyl transferase (TdT), which catalyzes polymerization of labeled nucleotides to free 3'-OH DNA ends in a template-independent manner (TUNEL-reaction). The TUNEL method (In Situ Cell Death Detection Kit, Fluorescein, Roche) combined with flow cytometry was used for the measurement of apoptosis (Gorczyca et al. *Cancer Res.* (1993), 53, 1945). The quantitative analysis of 3'-OH ends was performed using the MDADS analysis program (Beckman Coulter).

HIV-1 infected Hut/CCR5 cells were treated with 2 (0.5, 5, and 50 µM) for 3 days. The cells were fixed (in 4% paraformaldehyde in PBS, pH 7.4) and permeabilisated (0.1% Triton X-100 in 0.1% sodium citrate), The cells were then rinsed twice with PBS and labeled with 50 µL TUNEL reaction mixture (50 µL Enzyme solution +450 µL Label solution) for 60 min. at 37° C. in a humidified atmosphere in dark. The samples were rinsed with PBS three times and resuspended in 1 mL PBS containing 5 μg/mL of PI and 0.1% RNAse. Flow cytometry was performed on a FACScan cytometry. The red (PI) and green (fluorescein) fluorescence emissions from each cell were measured.

Figure 10:
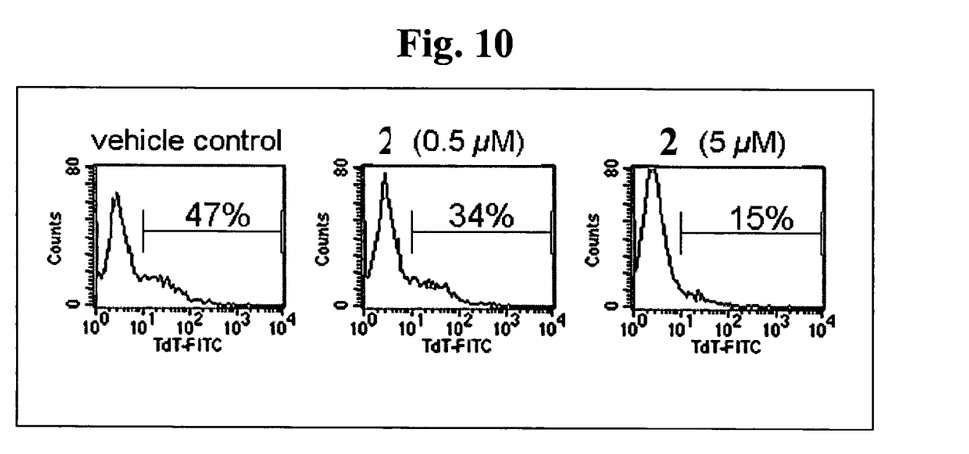
FIG. 10 illustrates the TUNEL assay showing that Na$_7$[Ru$_4$($\mu_3$-O)$_4$(C$_2$O$_4$)$_6$] (2) exhibits cytoprotective activity toward HIV-1 infected Hut/CCR5 cells in a 7-day incubation period.

$Na_7[Ru_4(\mu_3\text{-}O)_4(C_2O_4)_6]$ (2) of this invention showed cytoprotective activity in HIV-1 Infected Hut/CCR5 cells (see FIG. 10).

Example 8

Percentage Cell Viability of HIV-infected Hut/CCR5, GHOST/CXCR4 and PBMC Cells in the Presence of $Na_7[Ru_4(\mu_3\text{-}O)_4(C_2O_4)_6]$ (2)

Example 8 describes the procedures employed to examine the percentage cell viability of HIV-infected Hut/CCR5, GHOST/CXCR4 and PBMC cells in the presence of $Na_7[Ru_4(\mu_3\text{-}O)_4(C_2O_4)_6]$ (2) and the results of these studies.

Assays on the cell viability of Hut/CCR5, GHOST/CXCR4 and PBMC were conducted in 96-well flat-bottomed microtitre plates. The supplemented culture medium (90 μL, with fetal bovine serum (10%, v/v), L-glutamine (2 mM), penicillin (100 U/mL) and streptomycin (100 μg/mL)) with cells ($1\times10^6$ cells per mL) was added into a 96-well plate. Complex 2 with concentrations ranging from 0.5-100 μM dissolved in culture medium (10 μL) were subsequently added into each of the 96 wells. Control wells contained only supplemented media (100 μL). Microtitre plates were incubated at 37° C. in a 5% $CO_2$/95% air humidified atmosphere for 7 days. All the assays were run in parallel with a negative control (i.e., vehicle control) and a positive control with cisplatin as a cytotoxic agent.

Assessment of the cell viability was carried out using a modified method of Mosman based MTT assay. 10 μL of MTT solution (5 mg MTT/mL in 1×PBS) was added to each well and incubated for 4 h. This was followed by adding 100 μL solubilization buffer (10% SDS in 0.01 M HCl) to each well to lysis the cells and solubilize the blue formazan complex formed. After overnight incubation, the formation of formazan was measured by a microtitre plate reader (Perkin-Elmer Fusion™ α-FP) using an absorbance 580 nm filter. $IC_{50}$ of the complex was calculated as cell survival in a range of complex concentration relative to the untreated control.

Figure 11:
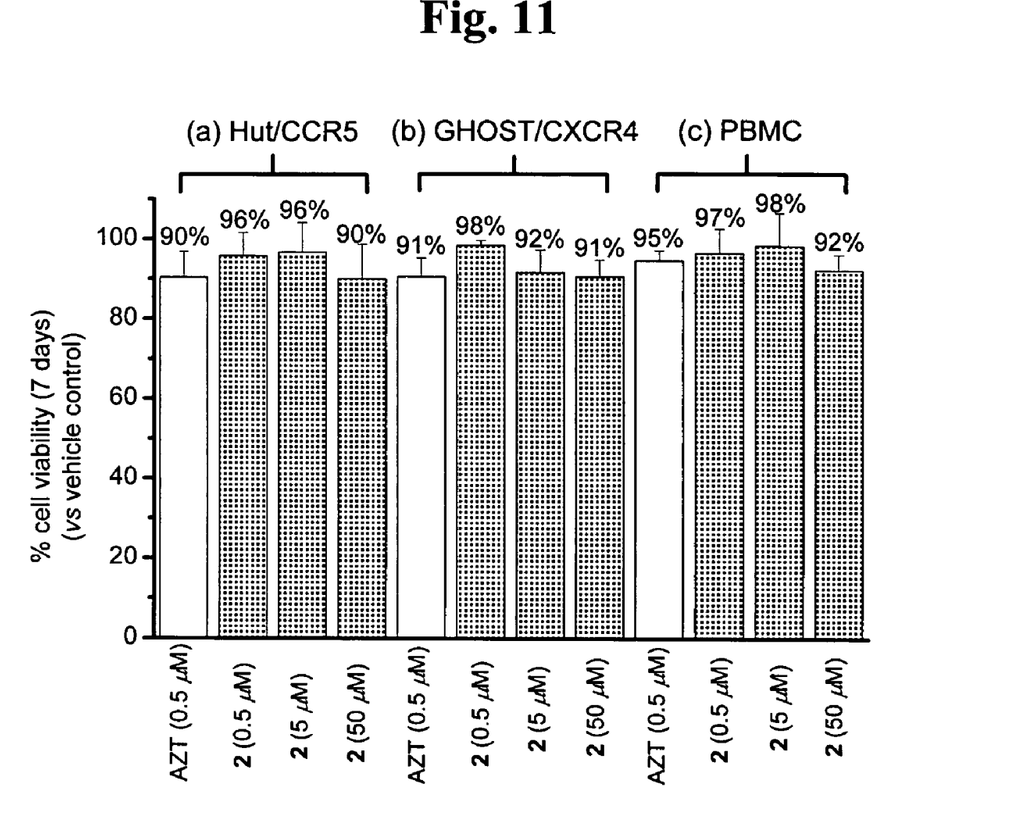
FIG. 11 illustrates the percentage cell viability of (a) Hut/CCR5 cells, (b) GHOST/CXCR4 cells and (c) PBMC in the presence of Na$_7$[Ru$_4$($\mu_3$-O)$_4$(C$_2$O$_4$)$_6$] (2).

$Na_7[Ru_4(\mu_3\text{-}O)_4(C_2O_4)_6]$ (2) of this invention showed an increase in cell viability/membrane rigidity of the HIV-1 infected Hut/CCR5, GHOST/CXCR4 and PBMC cells (see FIG. 11).

What is claimed is:

1. A method for the treatment of HIV comprising administering, to a patient in need thereof or into a cell-based assay, a composition comprising an effective amount of the following ruthenium oxalato cluster wherein X is a pharmaceutically acceptable counter-ion,
P is an integer from +1 to +3, and
n is equal to the absolute value of −7/p, and
a pharmaceutically acceptable carrier.

2. The method according to claim 1, wherein the composition is administered to a patient in need thereof.

3. The method according to claim 1, wherein the patient is a mammal.

4. The method according to claim 1, wherein the composition is administered into a cell-based assay.

5. The method according to claim 1, wherein the cell is a cell of a mammal.

6. The method according to claim 1, wherein the ruthenium oxalato cluster inhibits HIV-1 (BaL) replication in Hut/CCR5 cells.

7. The method according to claim 1, wherein the ruthenium oxalato cluster inhibits HIV-1 ($III_B$) replication on GHOST/CXCR4 cells.

8. The method according to claim 1, wherein the ruthenium oxalato cluster inhibits HIV-1($III_B$) replication on PBMC cells.

9. The method according to claim 1, wherein the ruthenium oxalato cluster is cytoprotective of HIV-1 infected Hut/CCR5 cells.

10. The method according to claim 1, wherein the ruthenium oxalate cluster inhibits reverse transcriptase activity.

11. The method of claim 2, wherein the composition is administered by injection.

* * * * *

UNITED STATES PATENT AND TRADEMARK OFFICE
CERTIFICATE OF CORRECTION

PATENT NO. : 7,648,977 B2 Page 1 of 1
APPLICATION NO. : 11/256175
DATED : January 19, 2010
INVENTOR(S) : Che et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1122 days.

Signed and Sealed this

Twenty-third Day of November, 2010

David J. Kappos
*Director of the United States Patent and Trademark Office*